United States Patent [19]

Nichols

[11] Patent Number: 5,209,932
[45] Date of Patent: May 11, 1993

[54] FOOT CARE COMPOSITIONS

[75] Inventor: Larry D. Nichols, Arlington, Mass.

[73] Assignee: Moleculon, Inc., Elizabeth, N.J.

[21] Appl. No.: 875,197

[22] Filed: Apr. 24, 1992

Related U.S. Application Data

[63] Continuation of Ser. No. 619,727, Nov. 29, 1990, abandoned, which is a continuation-in-part of Ser. No. 358,690, May 30, 1989, Pat. No. 5,000,947.

[51] Int. Cl.$^5$ .................... A01N 25/12; A01N 59/16; A61K 9/14
[52] U.S. Cl. .................................. 424/409; 424/488; 424/489; 424/499; 424/68; 424/642; 428/402.2; 514/781; 514/951
[58] Field of Search ............... 424/405, 409, 488, 489, 424/65, 68, 69

[56] References Cited

U.S. PATENT DOCUMENTS

| | | | |
|---|---|---|---|
| 3,824,085 | 7/1974 | Teng et al. | 44/78 |
| 3,846,404 | 11/1974 | Nichols | 260/230 |
| 3,846,404 | 11/1974 | Nichols | 260/230 |
| 3,940,384 | 2/1976 | Teng et al. | 260/226 |
| 3,985,298 | 10/1976 | Nichols | 239/54 |
| 4,016,254 | 4/1977 | Seager | 423/33 |
| 4,024,073 | 5/1977 | Shimizu et al. | 252/316 |
| 4,029,726 | 6/1977 | Nichols | 264/41 |
| 4,067,824 | 1/1978 | Teng et al. | 252/522 |
| 4,128,507 | 12/1978 | Mitzner | 252/522 |
| 4,193,989 | 3/1980 | Teng et al. | 424/60 |
| 4,369,173 | 1/1983 | Causland et al. | 424/35 |
| 4,382,919 | 5/1983 | Alonso et al. | 424/69 X |
| 4,383,988 | 5/1983 | Teng et al. | 424/68 |
| 4,597,960 | 7/1986 | Cohen | 424/28 |
| 4,643,856 | 2/1987 | Nichols | 264/41 |
| 4,690,786 | 9/1987 | Ninomiya et al. | 264/4.6 |
| 4,690,825 | 9/1987 | Won | 424/501 |
| 4,695,464 | 9/1987 | Aldermann | 424/449 |
| 4,708,821 | 11/1987 | Shimokawa et al. | 512/12 |
| 4,724,240 | 2/1988 | Abrutyn | 514/847 |
| 4,738,851 | 4/1988 | Schoenwald et al. | 424/488 |
| 4,752,496 | 6/1988 | Fellows et al. | 432/27 |
| 4,755,433 | 7/1988 | Patel et al. | 428/422 |
| 4,888,420 | 12/1989 | Steiner et al. | 536/64 |
| 4,925,667 | 5/1990 | Fellows et al. | 424/401 |
| 4,952,402 | 8/1990 | Sparks et al. | 424/419 |
| 5,000,947 | 3/1991 | Nichols | 424/69 |
| 5,013,473 | 5/1991 | Norbury et al. | 252/174.13 |

OTHER PUBLICATIONS

Moleculon, Inc., Form 10-K for FY ended Nov. 30, 1988, pp. 1-7.

Primary Examiner—Thurman K. Page
Assistant Examiner—Neil Levy
Attorney, Agent, or Firm—Thomas J. Engellenner; James E. Maslow

[57] ABSTRACT

Liquefiable and porous powder compositions are disclosed for the delivery of topical foot-care preparations. In particular, microporous cellulosic powders, such as cellulose acetates or nitrates, are disclosed as high liquid-content vehicles for the delivery of foot-care preparations. The resulting powders permit the application of the foot-care preparation by simply rubbing or otherwise applying the formulation onto the skin in such a manner that the powder liquefies and appears to vanish. Upon application, the frangible liquid-loaded cellulosic powders break up into minute particles that do not pass easily beyond the initial layers of the skin, but do permit the slow release of the foot-care preparation for absorption into the skin.

15 Claims, No Drawings

FOOT CARE COMPOSITIONS

REFERENCE TO RELATED APPLICATION

This application is a continuation of U.S. Ser. No. a continuation-in-part of U.S. Ser. No. 358,690 filed May 30, 1989, now U.S. Pat. No. 5,000,947.

BACKGROUND OF THE INVENTION

The technical field of this invention is personal skin care and, in particular, methods and materials for applying hygienic compositions to the feet.

Powders, such as talc or starch, have long been used to reduce the discomfort of fatigued or perspiring feet. These powders can be scented to mask foot odor. Also, these powders can be medicated to combat fungi and bacteria which cause foot odor and give rise to painful athletes foot infections.

Nonporous powders such as talc or starch can carry no more than about 5-15% of a foot-care liquid without caking and gumminess. Similarly the ability of nonporous powders to absorb liquids, including perspiration, is limited to the same 5-15% range.

Ideal compositions for use as foot-care preparations should be able to disperse easily onto the skin, carry a high payload of active ingredients, deliver that payload effectively to the entire area of application, and have the ability to absorb a large quantity of perspired moisture. The typical topical foot-care preparation includes a nonporous powder which does not satisfy these requirements. There therefore exists a need for better foot-care preparations capable of carrying greater payloads of foot-care agents while maintaining the ease of application inherent in powder compositions.

It is therefore an object of the present invention to provide foot-care preparations offering improved applicability, delivery and absorptivity.

SUMMARY OF THE INVENTION

Liquefiable powders and porous absorbant powders are disclosed as improved foot-care compositions. In particular, microporous cellulosic powders such as cellulose acetates or nitrates are disclosed both as high liquid content vehicles for the delivery of antimicrobials to the skin, and as dry porous powders for better absorption of perspiration. Distinct cellulosic powders offering these two complementary benefits can be blended into a single foot-care powder, and active agents which are well administered as powders, such as aluminum chlorhydrate based antiperspirants, can also be blended into such composite foot powder formulations. The resulting powders allow the simultaneous podiatric administration of active liquids, active powders, and perspiration-combating absorbants. Therefore, compositions made in accordance with the present invention overcome many of the limitations associated with conventional foot powders, thereby improving the effectiveness, convenience, and economy of such preparations.

Details of the formation of cellulosic powders can be found in the above-referenced parent application, U.S. Ser. No. 358,690, filed May 30, 1989 and now U.S. Pat. No. 5,000,947, and a commonly-owned, copending application entitled "Process For Producing Liquid-Loaded Powders", by Larry D. Nichols and John F. Cline, U.S. Ser. No. 07/619,736, filed contemporaneously herewith and now abandoned, both of which are incorporated herein by reference. A preferred liquid-loadable powder includes microporous cellulose triacetate prepared by the method of the above abandoned application U.S. Ser. No. 07/619,736.

In one technique, the liquefiable powders or dry porous powders are formed by dissolving a cellulosic polymer and possibly a pore-forming liquid in a volatile, polar solvent (e.g., a low molecular weight halogenated hydrocarbon, ester or diester) and then dispersively evaporating the solution, for example, by spray drying. Suitable volatile solvents for cellulosic polymers include methylene chloride, acetone, ethyl acetate, ethyl carbonate, methyl formate and the like. Methylene chloride is a preferred solvent when the cellulosic polymer is cellulose triacetate. Alternatively, other solvents, such as formic acid or the like, can be used and the resulting solution can be sprayed into a non-solvent such as methanol where the powder particles are then recovered by filtration and rinsing. The active agent can be incorporated into the solvent or introduced by liquid phase substitution after the powder is formed.

The cellulosic powders useful in the present invention can range from about one to about 500 micrometers in average diameter, preferably from about 5 to about 100 micrometers in average diameter, and typically are roughly microspherical in shape. They are further characterized by being microporous with interconnecting pores ranging in size from about one to about 500 nanometers and capable of holding liquid payloads of active agents.

The cellulosic powder can be formed from cellulosic polymers chosen from the group of cellulose acetates, cellulose butyrates, cellulose nitrates, cellulose propionates, ethyl celluloses and discrete or molecular mixtures thereof. One preferred cellulosic powder is a polymeric powder of cellulose triacetate, having a (dry) acetyl content greater than about 42 percent. The liquid content of the cellulosic powders of the present invention can range from about 50 percent to about 95 percent by weight.

Foot-care ingredients which can be used in the practice of the invention include but are not limited to antifungals such as tolnaftates and zinc undecylenates, disinfectants such as phenols and betadines, antiperspirants such as aluminum chlorhydrate, and deodorant fragrances, as well as derivatives or mixtures of such ingredients. Other active ingredients will occur to those skilled in the art, and may include compounds not yet approved or available. The cellulosic matrix of the liquefiable powders and porous powders of this invention is broadly compatible with a wide range of aqueous solutions, alcohols, and organic liquids, and foot-care agents have no deleterious effect on the powder matrix at concentrations consistent with use on the feet.

In some cases it may prove advantageous to include in the formulation inactive solvents, extenders or excipients. When excipients are to be used in the present invention, most standard topical and cosmetic components will be found suitable, including but not limited to talcs, starches, mineral oils, silicones, alcohols, glycols, esters and other organics known to be harmless to the skin.

In various embodiments of the invention, foot-care agents can be incorporated into liquid-containing cellulosic microbeads, incorporated into liquid-free porous cellulosic microbeads, or bulk-blended with such powders or mixtures of such powders. The resulting powders can then be used directly in powdered form, or mixed with other powders such as talc or starch, or compacted into cakes, or combined with binders and shaped into bars or sticks, or mixed into creams or lotions. In all such embodiments, the material after application to the feet is distributed substantially as a fragmented powder whose intimate contact with the skin allows very effective delivery of active ingredients and absorption of exudations from the skin.

In one embodiment of the invention, the frangible liquid-containing cellulosic microbeads can be formulated into a cream or lotion by admixture with a suitable liquid base. Such creams can be made as stable as conventional stabilized emulsions without the potentially irritating surface-active agents used to stabilize emulsions. Creams prepared from the cellulosic foot powders of this invention can thus provide particularly nonirritating, hypoallergenic lotions. Suitable liquid bases for cellulosic-powder creams or lotions include water, volatile alcohols, light oils, and volatile silicones.

Suitable liquid bases for cream or lotion type embodiments include water, oils and moisturizing agents, such as glycerin or aloe vera gels. Additional ingredients can include stearic acid, cyclic silicone liquids, triethanolamine, petrolatum, cetyl alcohol, carbomers, and the like.

Regardless of the embodiment, various additives can be mixed with the frangible cellulosic powders, whether dry, liquid-containing or a mixture of both, including, for example, talc, cornstarch, waxes, silicones, analgesics, cosmetics, fragrances, lubricants, emollients, moisturizers, medications and other personal care agents, colorants, pearlescent agents, and mixtures of such additives.

In the compacted cake embodiments, the liquid loaded powders can be compacted to yield cakes that are dry and firm and yet readily permit transfer of the formulation to the skin by finger or brush. Such compacted cakes can be obtained by applying a pressure ranging from about 50 to about 80 PSI to a cellulosic powder which has been appropriately loaded with a liquid payload of the active agent.

Sticks or bars incorporating liquefiable powder or dry porous powders with active agent payloads can be made by a variety of techniques. For example, sticks can be formulated by compounding a liquefiable powder or dry porous powder with fatty alcohols, fatty acids, and/or salts of fatty acid anions with metallic or alkanolamine cations to produce a stick having a soap as the binding agent.

Alternatively, stick compositions can be formed by compounding a liquefiable powder or dry porous powder with soft, water-soluble polymers, such as polyethylene glycols or polypropylene glycols, to produce a stick having a soluble wax as the binding agent. Sticks can also be made up by compounding a liquefiable powder or dry porour powder with silicones or with blends of liquids and solids, such as salts and/or propylene glycols, to produce sticks having a thick or partially-solidified slurry as the binding agent. In yet another approach, sticks can be formed by compounding a liquefiable powder or dry porous powder with a fusible wax, including fatty esters, silicone waxes, polyglycol waxes and aliphatic waxes, and then applying heat and pressure to produce sticks having a wax as the binding agent.

The above binding agents can be introduced directly, or as payload in a second portion of liquefiable powder or dry porous powder to be blended with that carrying the active ingredient. Other methods of stick production will readily occur to those skilled in the art and are consistent with practice of the present invention.

The invention will next be described in connection with certain exemplary methods and compositions. However, it should be clear that various additions, substractions and changes can be made by those skilled in the art without departing from the spirit or scope of the invention. For example, various additives can be mixed together with the dry and/or liquid loaded powder particles of the invention, including, for example, talc, cornstarch, waxes, silicones, cosmetics, fragrances, lubricants, emollients, moisturizers, medications and other personal care agents, as well as colorants, pearlescent agents, and mixtures of such additives.

In some applications, it may also be preferable to include a quantity of a dry cellulosic powder (e.g., less than 50 percent of the total cellulosic components) to provide additional structural integrity to the composition. The term "dry cellulosic powder" is used herein to describe powders whose internal pores are liquid-free or have a liquid content of less than 50 percent.

DETAILED DESCRIPTION

The examples below illustrate the preparation of liquefiable topical foot-care powders according to the invention.

EXAMPLE 1

A liquefiable powder was prepared by evaporative spray drying. Dow Corning 345, a slightly volatile cyclic silicone liquid, was used as the porogen. 40 grams of cellulose triacetate was dissolved in 3000 gm of methylene chloride by moderate stirring for 4 hours. To that solution was added 270 gm of the porogen dissolved in 1000 gm of methylene chloride. The resulting homogeneous solution was sprayed at 1000 PSI from a 0.0135" nozzle, downward into a tower 100 cm in diameter and 300 cm tall, through which 1250 liters per minute of solvent-free air was passing from top to bottom.

The evaporatively-formed powder was collected on a fabric filter spanning the bottom of the tower, and the solvent-laden air was passed through carbon beds to collect and recover solvent. The product was transferred to a steel tray and exposed as a 1 cm deep layer in a ventilated hood for 25 minutes to remove residual solvent. Analysis showed 12% cellulose triacetate, 88% DC 345, and less than 4 ppm of residual methylene chloride.

The white powder readily could be dusted onto the feet and made to liquefy and vanish by gentle rubbing. There was no perceptible grit or gumminess. The emollient silicone liquid feels refreshing to the feet at the time of application. Within an hour the silicone evaporates, leaving an imperceptible dry, absorbent residue of fragmented powder which effectively counters the effects of perspiration for a period of minutes to hours, depending on the amount of powder used and the level of exercise. EXAMPLE 2

A powder similar to that of Example 1 was prepared using as porogen a 0.1% solution of phenol in DC 345. The resulting white powder conveyed a perceptible antiseptic odor of phenol, and produced an astringent feeling on the feet.

EXAMPLE 3

A dry, absorbant, medicated cellulosic foot powder was prepared by spray evaporating a solution of 285 grams of cellulose triacetate and 15 grams of tolnaftate in 3000 grams of methylene chloride. The solution was sprayed at 1000 PSI from a 0.0135" nozzle, downward into a tower 100 cm in diameter and 300 cm tall, through which 1250 liters per minute of solvent-free air was passing from top to bottom.

The evaporatively-formed porous powder was collected on a fabric filter spanning the bottom of the tower, and the solvent-laden air was passed through carbon beds to collect and recover solvent. The product was transferred to a steel tray and exposed as a 1 cm deep layer in a ventilated hood for 25 minutes to remove residual solvent. Analysis showed 95% cellulose triacetate, 5% tolnaftate, and less than 1 ppm of residual methylene chloride. The bulk density of this powder was less than 0.15 gm/ml, indicative of a high degree of internal porosity.

EXAMPLE 4

9 grams of the dry powder of Example 3 was blended with 1 gram of micronized aluminum chlorhydrate powder. There was no perceptible change in the appearance or feel of the preparation when compared with chlorhydrate-free powder.

EXAMPLE 5

A dry powder similar to that of Example 3 was prepared without tolnaftate. 25 grams of that powder was tumbled in a miniature double-cone blender while 100 mg of sandalwood oil was introduced by atomization over a one minute period. The resulting fragrant powder was readily applicable to the feet, and imparted strong sandalwood odor.

EXAMPLE 6

Equal parts by weight of the medicated, liquid-containing powder of Example 2 and the deodorant powder of Example 5 were blended using a small laboratory vortex mixer. Rubbed on the feet the resulting powdered preparation provided the astringent emolliency of the phenol-containing powder, while the odor of phenol was masked by the sandalwood fragrance.

It will be understood that the above description pertains to only several embodiments of the present invention. That is, the description is provided by way of illustration and not by way of limitation. The invention will therefore will be further defined according to the following claims.

What is claimed is:

1. A foot-care composition for the delivery of a foot-care preparation, the composition comprising a formulation of a frangible, liquid-containing, cellulosic powder formed by spray evaporation and having particles ranging in average diameter from about 1 to about 500 micrometers, the particles further characterized by being microporous with a plurality interconnecting pores ranging in size from about 1 to about 500 nanometers and having a structure which is readily fragmented; and a liquid foot-care preparation loaded within the pores of the powder particles, such that the liquid-containing powder has a liquid content ranging from about 50 percent to 95 percent by weight and, upon application and rubbing, the rubbed particles fragment and the foot-care preparation is readily released.

2. The composition of claim 1 wherein the cellulosic powder is a polymeric powder chosen from the group consisting of cellulose acetates, cellulose butyrates, cellulose nitrates, cellulose propionates, ethyl celluloses, and discrete and molecular mixtures thereof.

3. The composition of claim 1 further comprising a dry, porous cellulosic powder.

4. A composition of claim 1 wherein the foot-care preparation includes an antifungal agent.

5. A composition of claim 4 wherein the antifungal agent is chosen from the group consisting essentially of tolnaftates, zinc undecylenates, derivatives and mixtures thereof.

6. A composition of claim 1 wherein the foot-care preparation includes a disinfectant.

7. A composition of claim 6 wherein the disinfectant is chosen from the group consisting essentially of phenols, betadines, derivatives and mixtures thereof.

8. A composition of claim 1 wherein the foot-care preparation includes an antiperspirant.

9. A composition of claim 8 wherein the antiperspirant is aluminum chlorhydrate.

10. The composition of claim 1 wherein the foot-care preparation is formulated as a solution or dispersion by mixing with an oil.

11. The composition of claim 10 wherein the oil is a mineral oil or silicone oil.

12. The composition of claim 1 wherein the foot-care preparation is formulated as a solution or dispersion by mixing with an emollient.

13. The composition of claim 12 wherein the emollient is from the group consisting essentially of isopropyl myristates and palmitates.

14. The composition of claim 12 further including a volatile solvent such as ethanol, isopropyl alcohol or other alcohol.

15. The composition of claim 12 wherein the emollient is not incorporated within the frangible powder.

* * * * *

UNITED STATES PATENT AND TRADEMARK OFFICE
CERTIFICATE OF CORRECTION

PATENT NO. : 5,209,932
DATED : May 11, 1993
INVENTOR(S) : Larry D. Nichols

It is certified that error appears in the above-identified patent and that said Letters Patent is hereby corrected as shown below:

On the title page, item [73] Assignee should read as follows:

--PUREPAC, INC., Elizabeth, N.J.--

Signed and Sealed this

Eleventh Day of January, 1994

*Attest:*

BRUCE LEHMAN

*Attesting Officer*  *Commissioner of Patents and Trademarks*